US011528910B2

(12) United States Patent
Van Der Lelie et al.

(10) Patent No.: US 11,528,910 B2
(45) Date of Patent: Dec. 20, 2022

(54) ***BACILLUS AMYLOLIQUEFACIENS* FCC1256 COMPOSITIONS AND METHODS OF CONTROLLING PLANT PATHOGENS**

(71) Applicant: FMC Corporation, Philadelphia, PA (US)

(72) Inventors: Daniel Van Der Lelie, Chapel Hill, NC (US); Safiyh Taghavi, Chapel Hill, NC (US); Anthony Andrew Devine, Rungsted Kyst (DK); Jaeheon Lee, Hellerup (DK)

(73) Assignee: FMC Corporation, Philadelphia, PA (US)

( * ) Notice: Subject to any disclaimer, the term of this patent is extended or adjusted under 35 U.S.C. 154(b) by 215 days.

(21) Appl. No.: 16/585,541

(22) Filed: Sep. 27, 2019

(65) Prior Publication Data

US 2020/0100504 A1 Apr. 2, 2020

Related U.S. Application Data

(60) Provisional application No. 62/738,653, filed on Sep. 28, 2018.

(51) Int. Cl.
*A01N 63/00* (2020.01)
*A01N 25/14* (2006.01)
*A01N 25/12* (2006.01)
*C12N 1/20* (2006.01)
*C12R 1/07* (2006.01)

(52) U.S. Cl.
CPC ............ *A01N 63/00* (2013.01); *A01N 25/12* (2013.01); *A01N 25/14* (2013.01); *C12N 1/205* (2021.05); *C12R 2001/07* (2021.05)

(58) Field of Classification Search
None
See application file for complete search history.

(56) References Cited

U.S. PATENT DOCUMENTS

2016/0186273 A1\* 6/2016 Taghavi ............... C05F 11/08
504/100

FOREIGN PATENT DOCUMENTS

| CN | 108004173 | 6/2021 | |
|---|---|---|---|
| WO | 2015/023662 A1 | 2/2015 | |
| WO | 2016/109395 A1 | 7/2016 | |
| WO | 2016/109396 A1 | 7/2016 | |
| WO | WO-2016156164 A1 \* | 10/2016 | ............ C12N 1/205 |

OTHER PUBLICATIONS

Montiero, F.P. et al. 2016. Effect of temperature, pH and substrate composition on production of lipopeptides by Bacillus amyloliquefaciens 629. African Journal of Microbiology Research 10(36): 1506-1512. specif. pp. 1506, 1507, 1509.\*
Zhang, H. 2009. Surfactant.Soft-Matter. Datasheet [online]. Retrieved: Dec. 30, 2021. Downloaded from the internet at: <soft-matter.seas. harvard. edu/index.php/Surfactant> pp. 1-7; specif. p. 1.\*
Extended European Search Report dated Dec. 7, 2018 issued in European Patent Application No. 18202293.9.

\* cited by examiner

*Primary Examiner* — Olivia M. Wise
*Assistant Examiner* — Sharon M. Papciak
(74) *Attorney, Agent, or Firm* — Armstrong Teasdale LLP

(57) ABSTRACT

Methods of controlling a plant pathogen, e.g. fungal and bacterial pathogens, on a plant, are described wherein an agricultural composition comprising *Bacillus amyloliquefaciens* FCC1256 deposited as ATCC No. PTA-122162, a carrier, a surface-active agent and optionally a buffer, and a corresponding concentrate is also described.

18 Claims, 2 Drawing Sheets

BACILLUS AMYLOLIQUEFACIENS FCC1256 COMPOSITIONS AND METHODS OF CONTROLLING PLANT PATHOGENS

CROSS-REFERENCE TO RELATED APPLICATION

This Application claims the benefit of U.S. Provisional Application 62/738,653 filed Sep. 28, 2018, the contents of which are herein incorporated by reference.

TECHNICAL FIELD

The presently disclosed subject matter relates to compositions comprising an isolated *Bacillus amyloliquefaciens* FCC1256 strain for application to plants or the soil surrounding plants to treat plant diseases caused by plant pathogens.

BACKGROUND

Fungal plant pathogens (phytopathogens), including but not limited to *Botrytis* spp., *Fusarium* spp., *Rhizoctonia* spp. are one type of plant pest that can cause severe economic losses in the agricultural and horticultural industries. Chemical agents can be used to control fungal phytopathogens, but the use of chemical agents suffers from disadvantages including high cost, lack of efficacy, emergence of resistant strains of the fungi, and undesirable environmental impacts. In addition, such chemical treatments tend to be indiscriminant and may adversely affect beneficial bacteria, fungi, and arthropods in addition to the plant pathogen at which the treatments are targeted. A second type of plant pest are bacterial plant pathogens, including but not limited to *Erwinia* spp., *Xanthomonas* spp., and *Pseudomonas* spp. that cause severe economic losses in the agricultural and horticultural industries. Similar to pathogenic fungi, the use of chemical agents to treat these bacterial pathogens suffers from disadvantages. Thus, microorganisms that can be applied as biopesticides to control pathogenic fungi and bacteria in plants are desirable and in high demand to improve agricultural sustainability.

Some members of the species *Bacillus* have been reported as biocontrol strains, and some have been applied in commercial products. For example, strains currently being used in commercial biocontrol products include: *Bacillus velezensis* QST713, used as the active ingredient of Serenade®, produced by Bayer Crop Science, and *Bacillus amyloliquefaciens* D747, used as the active ingredient in Double Nickel produced by Certis. In addition, *Bacillus* strains currently being used in commercial biostimulant products include: *Bacillus velezensis* FZB42 used as the active ingredient in RhizoVital® 42, produced by ABiTEP GmbH.

Moreover, WO 2016/109396 A1 discloses *Bacillus amyloliquefaciens* RTI472 for use in benefiting plant growth and for treating plant diseases like fungal and bacterial infections.

Further, WO 2016/109395 A1 discloses *Bacillus amyloliquefaciens* RTI301 for use in benefitting plant growth and for treating plant diseases like fungal and bacterial infections.

Also, WO 2015/023662 A1 discloses, i.a., a *Bacillus amyloliquefaciens* strain for inhibiting the growth and/or activity of fungal plant pathogens.

However, despite the availability of certain biological pesticides, there is a need in the art to improve specificity against the target diseases and their respective causal pathogens. Further, there is a need to improve efficacy and potency of biological pesticides which may be impacted by various biotic and abiotic factors. The present invention addresses the need in the art by providing novel microbial compositions and methods for their use to control the growth of plant pathogens and thereby alleviate or prevent plant diseases.

SUMMARY OF THE INVENTION

The present invention resides in the isolation of a new *Bacillus amyloliquefaciens* strain from strawberry plant soil. The strain of *Bacillus amyloliquefaciens* FCC1256 has been deposited at the ATCC under Patent Accession No. PTA-122162, cf. Example 1.

In at least one embodiment, the present invention is directed to methods of controlling plant pathogen(s) on a plant, the methods comprising the step of applying a composition comprising *Bacillus amyloliquefaciens* FCC1256 to the plant, to a part of the plant and/or to a locus at which the plant or plant part grows or is to be planted.

In another embodiment, the present invention relates to a method of controlling fungal plant pathogen(s) and/or bacterial plant pathogen(s) on a plant, the method comprising the step of applying a composition comprising *Bacillus amyloliquefaciens* FCC1256 to over-ground parts of the plant.

In one embodiment, an agricultural composition is provided comprising a) *Bacillus amyloliquefaciens* FCC1256, and b) an agriculturally suitable formulation medium, e.g. comprising a suitable carrier, a surface-active agent, and optionally a buffer. The agricultural composition is particularly useful for application to protect plants against pathogens or treat a pathogenic infection in a susceptible plant, e.g. according to the methods described herein. In some embodiments, the composition comprises iturin and fengycin in a relative ratio of in the range of from 1.3:1.0 to 3.0:1.0, such as from 1.5:1.0 to 2.8:1.0, respectively.

In further embodiments, a concentrate for an agricultural composition is provided, the concentrate comprising: a) *Bacillus amyloliquefaciens* FCC1256, and b) an agriculturally suitable formulation medium, e.g. a medium comprising a suitable carrier, a surface-active agent, and optionally a buffer.

BRIEF DESCRIPTION OF THE FIGURES

Figure 1:
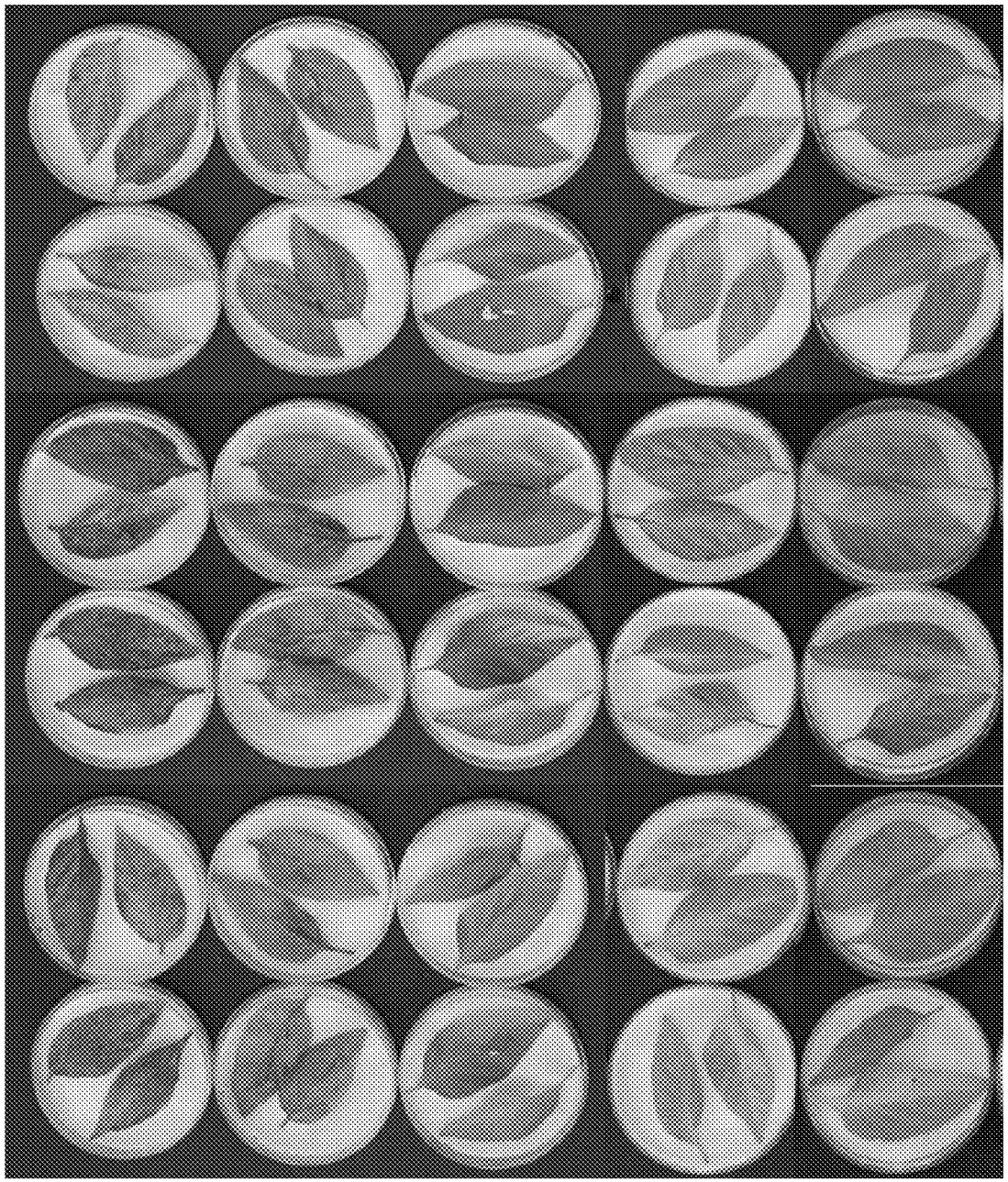

Having thus described the presently disclosed subject matter in general terms, reference will now be made to the accompanying Figures described in the following:

FIG. 1 shows the results of the Detached Pepper Leaf Disk assay comparing the activity of *Bacillus amyloliquefaciens* FCC1256 to untreated controls as well as to the commercial product Serenade® Optimum.

Figure 2:
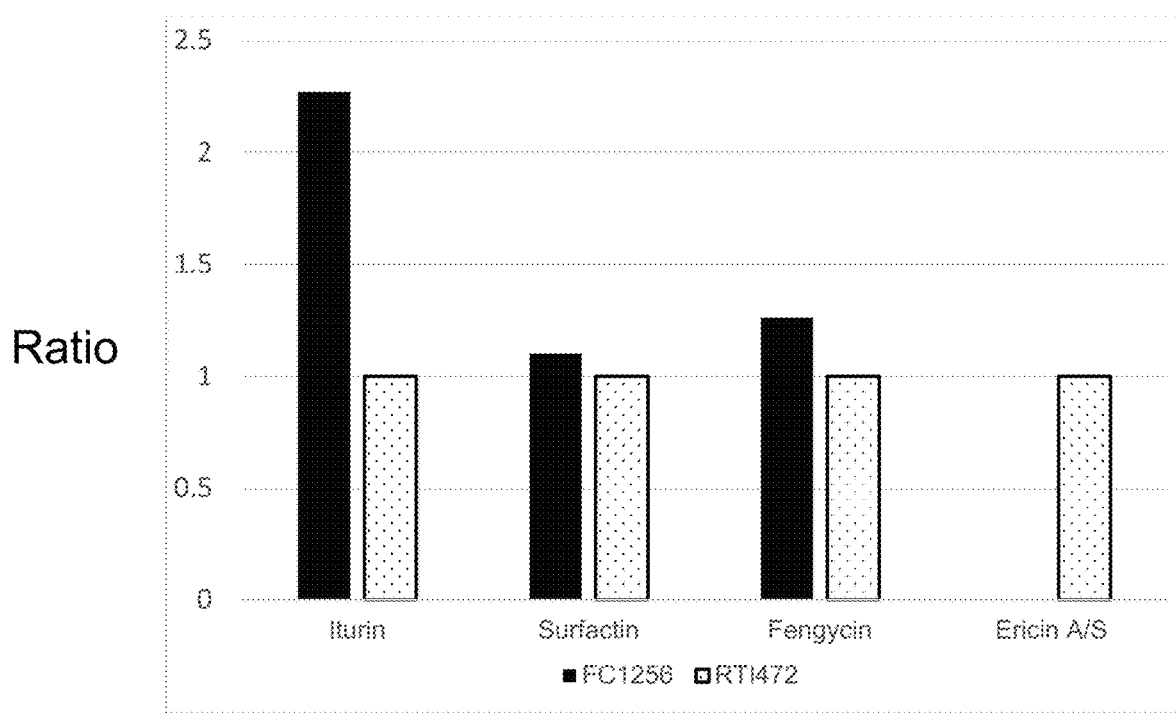

FIG. 2 shows the typical ratios of iturin, surfactin, fengycin and ericin A/S from FCC1256 and RTI472 cultures, respectively.

DETAILED DESCRIPTION

As used herein, the designations "*Bacillus amyloliquefaciens* FCC1256" and "FCC1256" refer to a biologically pure culture of the *Bacillus amyloliquefaciens* FCC1256 bacterial strain deposited under Patent Accession No. PTA-122162, cf. Example 1. In the methods, compositions, etc. described herein, the strain may be present in one or a combination of forms: as isolated spores of the bacterial stain, as a fermentation broth comprising spores of the bacterial strain, as a processed fermentation product comprising spores of the bacterial strain, as isolated vegetative cells of the bacterial strain, as a fermentation broth comprising vegetative cells of the bacterial strain, and as a processed fermentation product comprising vegetative cells of the bacterial strain.

The term "biologically pure culture" refers a laboratory or fermentation culture which contains a single species of organism, i.e. in the present case virtually exclusively a *Bacillus amyloliquefaciens* FCC1256 bacterial strain. This means that any other microorganisms involved in the fermentation broth of the pure culture are considered as contaminations, which only exist in a negligible amount and does not cause measurable changes to the physical and chemical compositions of the broth.

The term "processed fermentation product" refers to a downstream processed form thereof, including but not limited to a concentrate of the fermentation broth, solids of a filtered fermentation broth, a reconstituted fermentation broth concentrate, and a dried fermentation broth (e.g. freeze-dried or spray-dried).

In some embodiments, FCC1256 is present as a fermentation broth comprising spores of FCC1256 or a processed fermentation product comprising spores of FCC1256, such as a concentrate of a fermentation broth or a spray-dried fermentation broth.

The fact that a biologically pure culture of *Bacillus amyloliquefaciens* FCC1256 is included in the compositions and methods disclosed herein does not exclude that the compositions and methods, respectively may include other defined microbial strains, in particular other biologically pure microbial strains.

The terms "a," "an," and "the" refer to "one or more" when used in this application, including the claims. Thus, for example, reference to "a plant" includes a plurality of plants, unless the context clearly is to the contrary.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and claims, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

For the purposes of this specification and claims, the terms "metabolite" and "metabolites" are used in connection with compounds having antimicrobial activity that are produced by *Bacillus amyloliquefaciens* FCC1256, such as iturin, fengycin and surfactin. The metabolites referred to as "iturin", "fengycin" and "surfactin" each represent a class of rather similar molecular structures. In so far that reference is made to amounts or ratios of including iturin, fengycin and surfactin, the amount/ratio is intended to relate to the total amount (weight) of the respective metabolite. The amount can be determined by HPLC analysis using suitable commercial standards.

Methods of the Invention

In certain embodiments of the present invention, compositions and methods are provided that include *Bacillus amyloliquefaciens* FCC1256 for application to a plant for conferring protection against a pathogenic infection in a susceptible plant. By the methods of the present invention, the controlling a plant pathogen may be reflected in reduced pathogenic infection, improved resistance to plant pathogens (e.g. resistance to subsequent attacks), improved seedling vigor, improved root development, improved plant growth, improved plant health, increased yield, improved appearance, or a combination thereof.

Hence, the present invention i.a. relates to a method of controlling plant pathogen(s) on a plant, the method comprising the step of applying a composition comprising *Bacillus amyloliquefaciens* FCC1256 to the plant, to a part of the plant and/or to a locus at which the plant or plant part grows or is to be planted.

As used herein, the term "plant pathogen" refers to organisms that cause infectious disease in plants, including fungi, bacteria, viruses, viroids, virus-like organisms, oomycetes, phytoplasmas, protozoa, nematodes and parasitic plants. In some embodiments, plant pathogens are selected from fungi and bacteria. In one variant, plant pathogens are selected from fungal plant pathogens. In another variant, plant pathogens are selected from bacterial plant pathogens.

In another embodiment, the method includes applying the composition comprising *Bacillus amyloliquefaciens* FCC1256 to the plant, to a part of the plant and/or to a locus at which the plant or plant part grows or is to be planted to control plant pathogens selected from the group consisting of a rust fungus, a *Botrytis* spp. (like *Botrytis cinerea, Botrytis squamosal*), an *Erwinia* spp. (like *Erwinia carotovora, Erwinia amylovora*), a *Dickeya* spp. (like *Dickeya dadantii, Dickeya solani*), an *Agrobacterium* spp. (like *Agrobacterium tumefaciens, Agrobacterium tumefaciens*), a *Xanthomonas* spp. (like *Xanthomonas axonopodis, Xanthomonas campestris* pv. *carotae, Xanthomonas pruni, Xanthomonas arboricola, Xanthomonas oryzae* pv. *oryzae*), a *Xylella* spp. (like *Xylella fastidiosa*), a *Candidatus* spp. (like *Candidatus liberibacter*), a *Fusarium* spp. (like *Fusarium colmorum, Fusarium graminearum, Fusarium oxysporum, Fusarium oxysporum f.* sp. *cubense, Fusarium oxysporum f.* sp. *lycopersici, Fusarium virguliforme*), a *Sclerotinia* spp. (like *Sclerotinia sclerotiorum, Sclerotinia minor, Sclerotinia homeocarpa*), a *Cercospora/Cercosporidium* spp., an *Uncinula* spp. (like *Uncinula necator*), a *Podosphaera* spp. (like *Podosphaera leucotricha, Podosphaera clandestine*), a *Phomopsis* spp. (like *Phomopsis viticola*), an *Alternaria* spp. (like *Alternaria tenuissima, Alternaria porri, Alternaria alternate, Alternaria solani, Alternaria tenuis*), a *Pseudomonas* spp. (like *Pseudomonas syringae* pv. Tomato), a *Phytophthora* spp. (like *Phytophthora infestans, Phytophthora parasitica, Phytophthora sojae, Phytophthora capsici, Phytophthora cinnamon, Phytophthora fragariae, Phytophthora ramorum, Phytophthora palmivara, Phytophthora nicotianae*), a *Phakopsora* spp. (like *Phakopsora pachyrhizi, Phakopsora meibomiae*), an *Aspergillus* spp. (like *Aspergillus flavus, Aspergillus niger*), a *Uromyces* spp. (like *Uromyces appendiculatusi*), a *Cladosporium* spp. (like *Cladosporium herbarum*), a *Rhizopus* spp. (like *Rhizopus arrhizus*), a *Rhizoctonia* spp. (like *Rhizoctonia solani, Rhizoctonia zeae, Rhizoctonia oryzae, Rhizoctonia caritae, Rhizoctonia cerealis, Rhizoctonia crocorum, Rhizoctonia fragariae, Rhizoctonia ramicola, Rhizoctonia rubi, Rhizoctonia leguminicola*), a *Macropho-*

*mina* spp. (like *Macrophomina phaseolina*), a *Magnaporthe* spp. (like *Magnaporthe grisea, Magnaporthe oryzae*), a *Mycosphaerella* spp. (like *Mycosphaerella graminocola, Mycosphaerella fijiensis* (Black sigatoga), *Mycosphaerella pomi, Mycosphaerella citri*), a *Monilinia* spp. (like *Monilinia fruticola, Monilinia vacciniicorymbosi, Monilinia laxa*), a *Colletotrichum* spp. (like *Colletotrichum gloeosporiodes, Colletotrichum acutatum, Colletotrichum Candidum*), a *Diaporthe* (spp. *Diaporthe citri*), a *Corynespora* spp. (like *Corynespora Cassiicola*), a *Gymnosporangium* spp. (like *Gymnosporangium jumperi-virginianae*), a *Schizothyrium* spp. (like *Schizothyrium pomi*), a *Gloeodes* spp. (like *Gloeodes pomigena*), a *Botryosphaeria* spp. (like *Botryosphaeria dothidea*), a *Neofabraea* spp., a *Wilsonomyces* spp. (like *Wilsonomyces carpophilus*), a *Sphaerotheca* spp. (like *Sphaerotheca macularis, Sphaerotheca pannosa*), an *Erysiphe* spp., a *Stagonospora* spp. (like *Stagonospora nodorum*), a *Pythium* spp. (like *Pythium ultimum, Pythium aphanidermatum, Pythium irregularum, Pythium ulosum, Pythium lutriarium, Pythium sylvatium*), a *Venturia* spp. (like *Venturia inaequalis*), a *Verticillium* spp., a *Ustilago* spp. (like *Ustilago nuda, Ustilago maydis, Ustilago scitaminea*), a *Claviceps* spp. (like *Claviceps puprrea*), a *Tilletia* spp. (like *Tilletia tritici, Tilletia laevis, Tilletia horrid, Tilletia controversa*), a *Phoma* spp. (like *Phoma glycinicola, Phoma exigua, Phoma lingam*), a *Cocliobolus* spp. (like *Cocliobolus sativus*), a *Gaeumanomyces* spp. (*Gaeumanomyces gaminis*), a *Colleototricum* spp., a *Rhycosporium* spp. (like *Rhycosporium secalis*), a *Biopolaris* spp., a *Helminthosporium* spp. (like *Helminthosporium secalis, Helminthosporium maydis, Helminthosporium solai, Helminthosporium tritici-repentis*), and a combinations thereof, including any subspecies variants thereof.

In some embodiments, the method is adapted to control one or more plant pathogens selected from *Botrytis cinerea, Botrytis squaomas, Fusarium graminearum, Fusarium oxysporum, Fusarium viguliforme, Phytophthora infestans, Phytophthora parasitica, Phytophthora sojae, Phytophthora capsici, Phytophthora cinnamon, Phytophthora fragariae, Phytophthora ramorum, Phytophthora palmivara, Phytophthora nicotianae, Sclerotinia sclerotiorum, Sclerotinia minor, Sclerotinia homeocarpa, Aspergillus favus, Pseudomonas syringae* pv. Tomato, *Erwinia amylovara, Rhizoctonia solani, Xanthomonas euvesicatoria*, and any combinations thereof, including any subspecies variants thereof.

In some embodiments, the methods of the invention utilize a composition comprising *Bacillus amyloliquefaciens* FCC1256 to controls diseases caused by such plant pathogens as pepper Grey Mold (*Botrytis cinerea*), pepper *Phytophthora* Blight (*Phytophthora capsica*), Tomato *Fusarium* crown rot (*Fusarium* sp.), Apple Fire Blight (*Erwinia amylovora*), Tomato Bacterial Speck (*Pseudomonas syringae*), Pepper Bacterial Spot disease (*Xanthomonas euvesicatoria*), soybean damping off (*Rhizoctonia solani*).

As used herein, the phrase "controlling plant pathogen(s)" in the context of the methods and compositions of the present invention is intended to mean an at least 10% reduction of the growth of the plant pathogen(s) compared to corresponding conditions where the methods or the compositions are not utilized, e.g. in some embodiments an at least 30% reduction, or an at least 50% reduction, or an at least 70% reduction, or an at least 80% reduction, or an at least 90% reduction, or essentially an elimination of the growth. In the latter instance, the elimination of the growth may result in visual elimination of the plant pathogen(s). Examples 3, 5, 6 and 7 demonstrate types of methodologies for determination of the degree of control of various plant pathogens by utilizing *Bacillus amyloliquefaciens* FCC1256.

The methods and compositions according to the invention are useful to prevent or treat diseases caused by plant pathogens in a broad range of plant including, but not limited to, Corn, Sweet Corn, Seed Corn, Silage Corn, Field Corn, Rice, Wheat, Barley, Sorghum, Asparagus, Blueberry, Blackberry, Raspberry, Loganberry, Huckleberry, Cranberry, Gooseberry, Elderberry, Currant, Cane berry, Bush berry, Broccoli, Cabbage, Cauliflower, Brussels Sprouts, Collards, Kale, Mustard Greens, Kohlrabi, Cucumber, Cantaloupe, Melon, Muskmelon, Squash, Watermelon, Pumpkin, Eggplant, Onion, Garlic, Shallots, Orange, Grapefruit, Lemon, Tangerine, Tangelo, Pomelo, Pepper, Tomato, Ground Cherry, Tomatillo, Okra, Grape, Lettuce, Celery, Spinach, Parsley, Radicchio, Beans, Green beans, Snap beans, Shell beans, Soybeans, Dry Beans, Garbanzo beans, Lima beans, Peas, Chick peas, Split peas, Lentils, Canola, Castor, Coconut, Cotton, Flax, Oil Palm, Olive, Peanut, Rapeseed, Safflower, Sesame, Sunflower, Soybean, Apple, Crabapple, Pear, Quince, May haw, Carrot, Potato, Sweet Potato, Cassava, Beets, Ginger, Horseradish, Radish, Ginseng, Turnip, Apricot, Cherry, Nectarine, Peach, Plum, Prune, Strawberry, Almond, Pistachio, Pecan, Walnut, Filberts, Chestnut, Cashew, Beechnut, Butternut, Macadamia, Kiwi, Banana, (Blue) Agave, Grass, Turf grass, Poinsettia, Chestnuts, Oak, Maple, sugarcane, and sugar beet.

In some embodiments, the plant is soybean, bean, snap bean, wheat, cotton, corn, pepper, tomato, potato, cassava, grape, strawberry, banana, peanut, squash, pumpkin, eggplant, and cucumber.

In other embodiments, the plant is selected from apples, asparagus, bayberry, bearberry, blackberry, highbush and lowbush blue berry, chokecherry, currant, elderberry, gooseberry, huckleberry, lingonberry, loganberry, mulberry, pin cherry, raspberry, Salaberry, Saskatoon berry, sea buckthorn and wild raspberry, blackberry or raspberry, grapes, strawberry, fuzzy kiwifruit, broccoli, Chinese broccoli, broccoli raab, Brussel sprouts, cabbage, cauliflower, broccoli, collard, kale, kohlrabi, mizuna, mustard greens, mustard spinach and rape greens, onions, garlic, leeks, shallot and chives, celery, cantaloupe, Chinese was gourd, cucumber, edible gourd, melon, muskmelon, pumpkin, squash, watermelon, eggplant, ground cherry, okra, peppers, tomatillos and tomato.

In still other embodiments, the plant is selected from pepper, cucumbers, apples, asparagus, bananas, citrus, kiwi, melons, peaches, pears, pineapple, pome fruit, pomegranate, celery, onions, garlic, grapes, leaks, shallots, chives, broccoli, cabbage, cauliflower, cucurbits, tomatoes, potatoes, wheat, rice or soybeans.

In at least one embodiment of the methods of the invention, the composition is applied to the plant, to a part of the plant and/or to a locus at which the plant or plant part grows or is to be planted, e.g. foliage of the plant, bark of the plant, fruit of the plant, flowers of the plant, seed of the plant, roots of the plant, a cutting of the plant, a graft of the plant, soil or growth medium surrounding the plant; soil or growth medium before sowing seeds of the plant in the soil or growth medium; or soil or growth medium before planting the plant, the plant cutting, or the plant graft in the soil or growth medium.

In one variant, the invention relates to a method of controlling fungal plant pathogen(s) and/or bacterial plant pathogen(s) on a plant, the method comprising applying a composition comprising *Bacillus amyloliquefaciens* FCC1256 deposited as ATCC No. PTA-122162 to over-ground parts of the plant.

As used herein, the phrase "applying [ . . . ] to over-ground parts of a plant", and the like, refers to application of the composition to the plant by aiming at the stem(s), the leave(s), the flower(s) and/or the fruit(s) of the plant. In other embodiments, application is aimed at the locus at which the plant or plant parts grows or is to be planted, e.g. to root system of the plant or the soil around the roots system of the plant, or to the soil in which the plant (or plant parts) is to be planted; this collectively being referred to as "applying [ . . . ] to the soil around the plant".

Applying a composition comprising *Bacillus amyloliquefaciens* FCC1256 to the plant, to a part of the plant and/or to a locus at which the plant or plant part grows or is to be planted may be accomplished by any conventional means, e.g. by spray application, by dripping, by powdering (powder application), by application of a foam (foam application), etc.

For applications to over-ground parts of a plant, spray application or powder application may prove particularly interesting.

For applications to the soil around the plant, spray application, application by dripping, powder application and foam application may be interesting. In one variant, application to the soil around a plant is by in-furrow application by dripping or foam application in connection with seed planting.

In some embodiments, the pathogenic infection can be caused by one or a combination of:

Soybean rust fungi (*Phakopsora pachyrhizi, Phakopsora meibomiae*) and the plant is soybean;

Grey Mold (*Botrytis cinerea*) and the plant is grape, strawberry or pepper;

*Alternaria* spp. (e.g. *Alternaria solani*) and the plant is tomato or potato;

Bean Rust (*Uromyces appendiculatus*) and the plant is common bean;

*Microsphaera diffusa* (Soybean Powdery Mildew) and the plant is soybean;

*Mycosphaerella fijiensis* (Black sigatoga) or *Fusarium oxysporum f.* sp. *cubese* (Panama disease) and the plant is banana;

*Xanthomonas* spp. or *Xanthomonas oryzae* pv. *oryzae* and the plant is rice;

*Xanthomonas axonopodis* and the plant is cassava;

*Xanthomonas campestris* and the plant is tomato;

Powdery mildew and the plant is a cucurbit;

Southern White Mold and the plant comprises peanut;

Leaf spot (*Cercospora/Cercosporidium*) and the plant is peanut;

*Fusarium graminearum* (Wheat Head Scab) and the plant is wheat;

*Mycosphaerella graminicola* (*Septoria tritici* blotch) and the plant is wheat;

*Stagonospora nodorum* (glume blotch and *Septoria nodorum* blotch), and the plant is wheat;

*Erwinia amylovora*, and the plant is selected from apple, pear and other pome fruits;

*Venturia inaequalis*, and the plant is selected from apple, pear and other pome fruits;

*Sclerotinia sclerotiorum* (white mold) and the plant is snap bean or potato;

*Sclerotinia homeocarpa* (dollar spot) and the plant comprises turf grass; or

*Rhizoctonia solani* and the plant is selected from wheat, rice, turf grass, soybean, corn, legumes and vegetable crops.

In one variant of the above-mentioned embodiment, the plant pathogen(s) is(are) controlled by application of the composition to the over-ground parts of the plant.

In embodiments herein, the composition is applied in an effective amount. The term "effective amount" refers to an amount of the composition which is sufficient to control at least one plant pathogen.

In embodiments, the composition is applied such that the rate of *Bacillus amyloliquefaciens* FCC1256 is in the range of from $4.0 \times 10^9$ CFU/ha to $4.0 \times 10^{17}$ CFU/ha, such as $4.0 \times 10^{10}$ CFU/ha to $4.0 \times 10^{16}$ CFU/ha. Typically, *Bacillus amyloliquefaciens* FCC1256 is applied in the form of spores thereof, rather than vegetative cells.

In some embodiments of the method of the invention, the composition is in liquid form, and the *Bacillus amyloliquefaciens* FCC1256 is present in the composition at a concentration of from $1.0 \times 10^6$ CFU/mL to $1.0 \times 10^{12}$ CFU/mL, such as from $1.0 \times 10^7$ CFU/mL to $1.0 \times 10^{11}$ CFU/mL.

In embodiments where the applied composition is in liquid form, the composition may be in the form of a liquid formulation selected from suspensions, suspension concentrates (SC), oil dispersions (OD) and foams.

In other embodiments of the method of the invention, the composition is in solid form, and the *Bacillus amyloliquefaciens* FCC1256 is present in the composition at a concentration of from $1.0 \times 10^6$ CFU/g to $1.0 \times 10^{12}$ CFU/g, such as from $1.0 \times 10^7$ CFU/g to $1.0 \times 10^{11}$ CFU/g.

In embodiments where the applied composition is in solid form, the composition may be in the form of a formulation selected from dustable powders (DP), water-dispersible granules (WG) and wettable powders (WP).

In some embodiments, the applied composition comprises iturin and fengycin in a relative weight ratio of in the range of from 1.3:1.0 to 3.0:1.0, such as from 1.5:1.0 to 2.8:1.0 and all measurements within such ranges.

The nature, embodiments and variants of the composition comprising *Bacillus amyloliquefaciens* FCC1256 utilized in the method of the invention will be further described in the following under the heading "Agricultural compositions of the invention".

Agricultural Compositions of the Invention

The composition as described herein and the embodiments thereof further elaborated on in the following are particularly useful in the method described hereinabove, but are not limited to such application. The compositions described under the present heading are intended to be ready-to-use compositions. In some embodiments, it may be convenient to prepare concentrated compositions suited for dilution before use to arrive at the ready-to-use agricultural compositions, e.g. to reduce transportation costs or to prolong the shelf-life, etc. Such concentrated formulations are described further below under the heading "Concentrates for agricultural compositions".

Hence, the present invention i.a. relates to an agricultural composition comprising: a) *Bacillus amyloliquefaciens*, and b) an agriculturally suitable formulation medium.

The term "agriculturally suitable" is intended to mean that the formulation medium as such (i.e. without any deliberate inclusion of further active ingredients) should not have significant detrimental effects on the plant or plants to which the agricultural composition is intended to be applied. Accordingly, "agriculturally suitable formulation medium" include any such formulation medium in which *Bacillus*

*amyloliquefaciens* FCC1256 can be placed in to facilitate transport of an effective amount to be applied to the plant part of interest, and which is otherwise suitable for agricultural use.

The formulation medium may include a liquid or solid carrier, as well as one or more additional components selected from surface-active agents, preservatives, humectants, desiccants, anti-foam agents, anti-freeze agents, dispersants, binders, emulsifiers, dyes, ultra-violet light protectants, drift-control agents, spray deposition aids, free-flow agents, buffers, and thickeners, and combinations thereof.

Examples of liquid carriers include water, animal oils and derivatives, mineral oils and derivatives, vegetable oils and derivatives, alcohols, polyols, triglycerides, natural and synthetic polymers and nonionic derivatives thereof. Examples of solid carriers include minerals, clays, silicas, inorganic and organic salts, sugars, starch, waxes, ground animal shells, botanical material including fibers, husks shells and flour.

In embodiments, the formulation medium comprises a suitable carrier and a surface-active agent. In variants hereof, the formulation medium further comprises a buffer.

In some embodiment, the agricultural composition comprises iturin and fengycin in a relative weight ratio of in the range of from 1.3:1.0 to 3.0:1.0, such as from 1.5:1.0 to 2.8:1.0, including all measurements within such ranges.

In some embodiments, the composition may be in the form of a formulation selected from suspensions, suspension concentrates (SC), oil dispersions (OD), foams, dustable powders (DP), water-dispersible granules (WG) and wettable powders (WP).

Typically, *Bacillus amyloliquefaciens* FCC1256 is included in suitable formulations in the form of spores thereof, rather than in the form of vegetative cells. For example, the formulations may include an aliquot of a fermentation broth comprising spores of FCC1256 or a processed fermentation product comprising spores of FCC1256, such as a concentrate of a fermentation broth or a spray-dried fermentation broth.

In some embodiments, the agricultural composition is in liquid form, and the *Bacillus amyloliquefaciens* FCC1256 is present in the composition at a concentration of from $1.0 \times 10^6$ CFU/mL to $1.0 \times 10^{12}$ CFU/mL, such as from $1.0 \times 10^7$ CFU/mL to $1.0 \times 10^{11}$ CFU/mL.

In embodiments where the agricultural composition is in liquid form, the composition may be in the form of a formulation selected from suspensions, suspension concentrates (SC), oil dispersions (OD) and foams.

In other embodiments, the agricultural composition is in solid form, and the *Bacillus amyloliquefaciens* FCC1256 is present in the composition at a concentration of from $1.0 \times 10^6$ CFU/g to $1.0 \times 10^{12}$ CFU/g, such as from $1.0 \times 10^7$ CFU/g to $1.0 \times 10^{11}$ CFU/g.

In embodiments where the agricultural composition is in solid form, the composition may be in the form of a formulation selected from dustable powders (DP), water-dispersible granules (WG) and wettable powders (WP).

In the methods for delivering FCC1256 in combination with a microbial, a biological, or a chemical insecticide, fungicide, nematicide, bacteriocide, or plant growth regulator, the composition can be in the form of a liquid, an oil dispersion, a dust, a dry wettable powder, a spreadable granule, or a dry wettable granule.

In some embodiments, the agricultural compositions may, in addition to the formulation medium, further include one or a combination of a microbial or a chemical insecticide, fungicide, nematicide, bacteriocide, plant growth regulator, or plant growth promotor, e.g.:

Insecticides: A0) various insecticides, including agrigata, al-phosphide, amblyseius, aphelinus, aphidius, aphidoletes, artimisinin, Autographa Californica NPV, azocyclotin, *Bacillus subtilis, Bacillus thuringiensis* spp. *aizawai, Bacillus thuringiensis* spp. *kurstaki, Bacillus thuringiensis, Beauveria bassiana*, beta-cyfluthrin, bisultap, brofluthrinate, bromophos-e, bromopropylate, capsaicin, cartap, celastrus-extract, chlorbenzuron, chlorethoxyfos, chlorfluazuron, cnidiadin, cryolite, cyanophos, cyhalothrin, cyhexatin, cypermethrin, dacnusa, DCIP, dichloropropene, dicofol, diglyphus, diglyphus+dacnusa, dimethacarb, emamectin, encarsia, EPN, eretmocerus, ethylene-dibromide, eucalyptol, fenazaquin, fenobucarb (BPMC), fenpyroximate, flubrocythrinate, flufenzine, formetanate, formothion, furathiocarb, gamma-cyhalothrin, garlic-juice, granulosis-virus, harmonia, heliothis armigera NPV, indol-3-ylbutyric acid, iodomethane, iron, isocarbofos, isofenphos, isofenphos-m, isoprocarb, isothioate, lindane, liuyangmycin, matrine, mephosfolan, metaldehyde, metarhizium-anisopliae, methamidophos, metolcarb (MTMC), mirex, m-isothiocyanate, monosultap, myrothecium verrucaria, naled, neochrysocharis formosa, nicotine, nicotinoids, omethoate, orius, oxymatrine, paecilomyces, parathion-e, pasteuria, pheromones, phosphorus-acid, photorhabdus, phoxim, phytoseiulus, pirimiphos-e, *Plutella xylostella* GV, polyhedrosis-virus, polyphenol-extracts, potassium-oleate, profenofos, prosuler, prothiofos, pyraclofos, pyrethrins, pyridaphenthion, pyrimidifen, pyriproxifen, quillay-extract, quinomethionate, rotenone, saponin, saponozit, sodium-fluosilicate, ssulfluramid, sulphur, tebupirimfos, tefluthrin, temephos, tetradifon, thiofanox, thiometon, transgenics (e.g., Cry3Bb1), triazamate, trichoderma, trichogramma, triflumuron, verticillium, vertrine, kappa-bifenthrin, kappa-tefluthrin, dichoromezotiaz, broflanilide, pyrazifumid; A1) the class of carbamates, including aldicarb, alanycarb, benfuracarb, carbaryl, carbofuran, carbosulfan, methiocarb, methomyl, oxamyl, pirimicarb, propoxur and thiodicarb; A2) the class of organophosphates, including acephate, azinphos-ethyl, azinphos-methyl, chlorfenvinphos, chlorpyrifos, chlorpyrifos-methyl, demeton-S-methyl, diazinon, dichlorvos/DDVP, dicrotophos, dimethoate, disulfoton, ethion, fenitrothion, fenthion, isoxathion, malathion, methamidophos, methidathion, mevinphos, monocrotophos, oxymethoate, oxydemeton-methyl, parathion, parathion-methyl, phenthoate, phorate, phosalone, phosmet, phosphamidon, pirimiphos-methyl, quinalphos, terbufos, tetrachlorvinphos, triazophos and trichlorfon; A3) the class of cyclodiene organochlorine compounds such as endosulfan; A4) the class of fiproles, including ethiprole, fipronil, pyrafluprole and pyriprole; A5) the class of neonicotinoids, including acetamiprid, clothianidin, dinotefuran, imidacloprid, nitenpyram, thiacloprid and thiamethoxam; A6) the class of spinosyns such as spinosad and spinetoram; A7) chloride channel activators from the class of mectins, including abamectin, emamectin benzoate, ivermectin, lepimectin and milbemectin; A8) juvenile hormone mimics such as hydroprene, kinoprene, methoprene, fenoxycarb and pyriproxyfen; A9) selective homopteran feeding blockers such as pymetrozine, flonicamid and pyrifluquinazon; A10) mite growth inhibitors such as clofentezine, hexythiazox and etoxazole; A11) inhibitors of mitochondrial ATP synthase such as diafenthiuron, fenbutatin oxide and propargite; uncouplers of oxidative phosphorylation such as chlorfenapyr; A12) nicotinic acetylcholine receptor channel blockers such as bensultap, cartap hydrochloride, thiocyclam and thiosultap sodium; A13) inhibitors of the chitin biosynthesis type 0 from the benzoylurea class, including bistrifluron, diflubenzuron, flufenoxuron, hexaflumuron, lufenuron, novaluron and teflubenzuron; A14) inhibitors of the chitin biosynthesis type 1 such as buprofezin; A15) moulting disruptors such as cyromazine; A16) ecdyson receptor agonists such as methoxyfenozide, tebufenozide, halofenozide and chromafenozide; A17) octopamin receptor agonists such as amitraz; A18) mitochondrial complex electron transport inhibitors pyridaben, tebufenpyrad, tolfenpyrad, flufenerim, cyenopyrafen, cyflumetofen, hydramethylnon, acequinocyl or fluacrypyrim;A19) voltage-dependent sodium channel blockers such as indoxacarb and metaflumizone; A20) inhibitors of the lipid synthesis such as spirodiclofen, spiromesifen and spirotetramat; A21) ryanodine receptor-modulators from the class of diamides, including flubendiamide, the phthalamide compounds (R)-3-Chlor-N1-{2-methyl-4-[1,2,2,2-tetrafluor-1-(trifluormethyl)ethyl]phenyl}-N2-(1-methyl-2-methylsulfonylethyl)phthalamid and (S)-3-Chlor-N1-{2-methyl-4[1,2,2,2-tetrafluor-1-(trifluormethyl)ethyl]phenyl}-N2-(1-methyl-2-methylsulfonylethyl)phthalamid, chlorantraniliprole and cyantraniliprole; A22) compounds of unknown or uncertain mode of action such as azadirachtin, amidoflumet, bifenazate, fluensulfone, piperonyl butoxide, pyridalyl, sulfoxaflor; or A23) sodium channel modulators from the class of pyrethroids, including acrinathrin, allethrin, bifenthrin, cyfluthrin, lambda-cyhalothrin, cypermethrin, alpha-cypermethrin, beta-cypermethrin, zeta-cypermethrin, deltamethrin, esfenvalerate, etofenprox, fenpropathrin, fenvalerate, flucythrinate, tau-fluvalinate, permethrin, silafluofen and tralomethrin.

Fungicides/bacteriocides: B0) benzovindiflupyr, anitiperonosporic, ametoctradin, amisulbrom, copper salts (e.g., copper hydroxide, copper oxychloride, copper sulfate, copper persulfate), boscalid, thiflumazide, flutianil, furalaxyl, thiabendazole, benodanil, mepronil, isofetamid, fenfuram, bixafen, fluxapyroxad, penflufen, sedaxane, coumoxystrobin, enoxastrobin, flufenoxystrobin, pyraoxystrobin, pyrametostrobin, triclopyricarb, fenaminstrobin, metominostrobin, pyribencarb, meptyldinocap, fentin acetate, fentin chloride, fentin hydroxide, oxytetracycline, chlozolinate, chloroneb, tecnazene, etridiazole, iodocarb, prothiocarb, *Bacillus subtilis*, extract from *Melaleuca alternifolia*, extract from *Lupinus albus* doce, BLAD polypeptide, pyrisoxazole, oxpoconazole, etaconazole, fenpyrazamine, naftifine, terbinafine, validamycin, pyrimorph, valifenalate, fthalide, probenazole, isotianil, laminarin, extract from *Reynoutria sachalinensis*, phosphorous acid and salts, teclofthalam, triazoxide, pyriofenone, organic oils, potassium bicarbonate, chlorothalonil, fluoroimide; B1) azoles, including bitertanol, bromuconazole, cyproconazole, difenoconazole, diniconazole, enilconazole, epoxiconazole, fluquinconazole, fenbuconazole, flusilazole, flutriafol, hexaconazole, imibenconazole, ipconazole, metconazole, myclobutanil, penconazole, propiconazole, prothioconazole, simeconazole, triadimefon, triadimenol, tebuconazole, tetraconazole, triticonazole, prochloraz, pefurazoate, imazalil, triflumizole, cyazofamid, benomyl, carbendazim, thiabendazole, fuberidazole, ethaboxam, etridiazole and hymexazole, azaconazole, diniconazole-M, oxpoconazol, paclobutrazol, uniconazol, 1-(4-chloro-phenyl)-2-([1,2,4]triazol-1-yl)-cycloheptanol and imazalilsulfphate; B2) strobilurins, including azoxystrobin, dimoxystrobin, enestroburin, fluoxastrobin, kresoxim-methyl, methominostrobin, orysastrobin, picoxystrobin, pyraclostrobin, trifloxystrobin, enestroburin, methyl (2-chloro-5-[1-(3-methylbenzyloxyimino)ethyl]benzyl)carbamate, methyl (2-chloro-5-[1-(6-methylpyridin-2-ylmethoxyimino)ethyl]benzyl)carbamate and methyl 2-(ortho-(2,5-dimethylphenyloxymethylene)-phenyl)-3-methoxyacrylate, 2-(2-(6-(3-chloro-2-methyl-phenoxy)-5-fluoro-pyrimidin-4-yloxy)-phenyl)-2-methoxyimino-N-methyl-acetamide and 3-methoxy-2-(2-(N-(4-methoxyphenyl)-cyclopropanecarboximidoylsulfanylmethyl)-phenyl)-acrylic acid methyl ester; B3) carboxamides, including carboxin, benalaxyl, benalaxyl-M, fenhexamid, flutolanil, furametpyr, mepronil, metalaxyl, mefenoxam, ofurace, oxadixyl, oxycarboxin, penthiopyrad, isopyrazam, thifluzamide, tiadinil, 3,4-dichloro-N-(2-cyanophenyl)isothiazole-5-carboxamide, dimethomorph, flumorph, flumetover, fluopicolide (picobenzamid), zoxamide, carpropamid, diclocymet, mandipropamid, N-(2-(4-[3-(4-chlorophenyl)prop-2-ynyloxy]-3-methoxyphenyl)ethyl)-2-methanesulfonyl-amino-3-methylbutyramide, N-(2-(4-[3-(4-chloro-phenyl)prop-2-ynyloxy]-3-methoxy-phenyl)ethyl)-2-ethanesulfonylamino-3-methylbutyramide, methyl 3-(4-chlorophenyl)-3-(2-isopropoxycarbonyl-amino-3-methyl-butyrylamino)propionate, N-(4'-bromobiphenyl-2-yl)-4-difluoromethyl-methylthiazole-δ-carboxamide, N-(4'-trifluoromethyl-biphenyl-2-yl)-4-difluoromethyl-2-methylthiazole-5-carboxamide, N-(4'-chloro-3'-fluorobiphenyl-2-yl)-4-difluoromethyl-2-methyl-thiazole-5-carboxamide, N-(3\4'-dichloro-4-fluorobiphenyl-2-yl)-3-difluoro-methyl-1-methyl-pyrazole-4-carboxamide, N-(3',4'-dichloro-5-fluorobiphenyl-2-yl)-3-difluoromethyl-1-methylpyrazole-4-carboxamide, N-(2-cyano-phenyl)-3,4-dichloroisothiazole-5-carboxamide, 2-amino-4-methylthiazole-5-carboxanilide, 2-chloro-N-(1,1,3-trimethylindan-4-yl)-nicotinamide, N-(2-(1,3-dimethylbutyl)-phenyl)-1,3-dimethyl-5-fluoro-1H-pyrazole-4-carboxamide, N-(4'-chloro-3',5-difluoro-biphenyl-2-yl)-3-difluoromethyl-1-methyl-1H-pyrazole-4-carboxamide, N-(4'-chloro-3',5-difluoro-biphenyl-2-yl)-3-trifluoromethyl-1-methyl-1H-pyrazole-4-carboxamide, N-(3',4'-dichloro-5-fluoro-biphenyl-2-yl)-3-trifluoromethyl-1-methyl-1H-pyrazole-4-carboxamide, N-(3',5-difluoro-4'-methyl-biphenyl-2-yl)-3-difluoromethyl-1-methyl-1H-pyrazole-4-carboxamide, N-(3',5-difluoro-4'-methyl-biphenyl-2-yl)-3-trifluoromethyl-1-methyl-1H-pyrazole-4-carboxamide, N-(cis-2-bicyclopropyl-2-yl-phenyl)-3-difluoromethyl-1-methyl-1H-pyrazole-4-carboxamide, N-(trans-2-bicyclopropyl-2-yl-phenyl)-3-difluoro-methyl-1-methyl-1H-pyrazole-4-carboxamide, fluopyram, N-(3-ethyl-3,5-5-trimethyl-cyclohexyl)-3-formylamino-2-hydroxy-benzamide, oxytetracyclin, silthiofam, N-(6-methoxy-pyridin-3-yl) cyclopropane-carboxamide, 2-iodo-N-phenyl-benzamide, N-(2-bicyclo-propyl-2-yl-phenyl)-3-difluormethyl-1-methylpyrazol-4-ylcarboxamide; B4) heterocyclic compounds, including fluazinam, pyrifenox, bupirimate, cyprodinil, fenarimol, ferimzone, mepanipyrim, nuarimol, pyrimethanil, triforine, fenpiclonil, fludioxonil, aldimorph, dodemorph, fenpropimorph, tridemorph, fenpropidin, iprodione, procymidone, vinclozolin, famoxadone, fenamidone, octhilinone, probenazole, 5-chloro-7-(4-methyl-piperidin-1-yl)-6-(2,4,6-trifluorophenyl)-[1,2,4]triazolo[1,5-a]pyrimidine, anilazine, diclomezine, pyroquilon, proquinazid, tricyclazole, 2-butoxy-6-iodo-3-propylchromen-4-one, acibenzolar-S-methyl, captafol, captan, dazomet, folpet, fenoxanil, quinoxyfen, N,N-dimethyl-3-(3-bromo-6-fluoro-2-methylindole-1-sulfonyl)-[1,2,4]triazole-1-sulfonamide, 5-ethyl-6-octyl-[1,2,4]triazolo[1,5-a]pyrimidin-2,7-diamine, 2,3,5,6-tetrachloro-4-methanesulfonyl-pyridine, 3,4,5-trichloro-pyridine-2,6-di-carbonitrile, N-(1-(5-bromo-3-chloro-pyridin-2-yl)-ethyl)-2,4-dichloro-nicotinamide, N-((5-bromo-3-chloropyridin-2-yl)-methyl)-2,4-dichloro-nicotinamide, diflumetorim, nitrapyrin, dodemorphacetate, fluoroimid, blasticidin-S, chinomethionat, debacarb, difenzoquat, difenzoquat-methylsulphat, oxolinic acid and piperalin; B5) carbamates, including mancozeb, maneb, metam, methasulphocarb, metiram, ferbam, propineb, thiram, zineb, ziram, diethofencarb, iprovalicarb, benthiavalicarb, propamocarb, propamocarb hydrochlorid, 4-fluorophenyl N-(1-(1-(4-cyanophenyl)-ethanesulfonyl)but-2-yl)carbamate, methyl 3-(4-chloro-phenyl)-3-(2-isopropoxycarbonylamino-3-methyl-butyrylamino)propanoate; or B6) other fungicides, including guanidine, dodine, dodine free base, iminoctadine, guazatine, kasugamycin, oxytetracyclin and its salts, streptomycin, polyoxin, validamycin A, binapacryl, dinocap, dinobuton, dithianon, isoprothiolane, fentin salts, edifenphos, iprobenfos, fosetyl, fosetyl-aluminum, phosphorous acid and its salts, pyrazophos, tolclofos-methyl, dichlofluanid, flusulfamide, hexachloro-benzene, phthalide, pencycuron, quintozene, thiophanate, thiophanate-methyl, tolylfluanid, cyflufenamid, cymoxanil, dimethirimol, ethirimol, furalaxyl, metrafenone and spiroxamine, guazatine-acetate, iminoctadine-triacetate, iminoctadine-tris(albesilate), kasugamycin hydrochloride hydrate, dichlorophen, pentachlorophenol and its salts, N-(4-chloro-2-nitro-phenyl)-N-ethyl-4-methyl-b enzenesulfonamide, dicloran, nitrothal-isopropyl, tecnazen, biphenyl, bronopol, diphenylamine, mildiomycin, oxincopper, prohexadione calcium, N-(cyclopropylmethoxy-imino-(6-difluoromethoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluormethyl-4-(3-trimethylsilanyl-propoxy)-phenyl)-N-ethyl-N-methylformamidine, N'-(5-difluormethyl-2-methyl-4-(3-trimethylsilanyl-propoxy)-phenyl)-N-ethyl-N-methyl formamidine, and fluindapyr.

Nematicides: C1) Benomyl, cloethocarb, aldoxycarb, tirpate, diamidafos, fenamiphos, cadusafos, dichlofenthion, ethoprophos, fensulfothion, fosthiazate, heterophos, isamidofof, isazofos, phosphocarb, thionazin, imicyafos, mecarphon, acetoprole, benclothiaz, chloropicrin, dazomet, fluensulfone, 1,3-dichloropropene (telone), dimethyl disulfide, metam sodium, metam potassium, metam salt (all MITC generators), methyl bromide, biological soil amendments (e.g., mustard seeds, mustard seed extracts), steam fumigation of soil, allyl isothiocyanate (AITC), dimethyl sulfate, furfual (aldehyde).

Plant growth regulators: D1) Antiauxins, such as clofibric acid, 2,3,5-tri-iodobenzoic acid; D2) Auxins such as 4-CPA, 2,4-D, 2,4-DB, 2,4-DEP, dichlorprop, fenoprop, IAA, IBA, naphthaleneacetamide, a-naphthaleneacetic acids, 1-naphthol, naphthoxyacetic acids, potassium naphthenate, sodium naphthenate, 2,4,5-T; D3) cytokinins, such as 2iP, benzyladenine, 4-hydroxyphenethyl alcohol, kinetin, zeatin; D4) defoliants, such as calcium cyanamide, dimethipin, endothal, ethephon, merphos, metoxuron, pentachlorophenol, thidiazuron, tribufos; D5) ethylene inhibitors, such as aviglycine, 1-methylcyclopropene; D6) ethylene releasers, such as ACC, etacelasil, ethephon, glyoxime; D7) gametocides, such as fenridazon, maleic hydrazide; D8) gibberellins, such as gibberellins, gibberellic acid; D9) growth inhibitors, such as abscisic acid, ancymidol, butralin, carbaryl, chlorphonium, chlorpropham, dikegulac, flumetralin, fluoridamid, fosamine, glyphosine, isopyrimol, jasmonic acid, maleic hydrazide, mepiquat, piproctanyl, prohydrojasmon, propham, tiaojiean, 2,3,5-tri-iodobenzoic acid; D10) morphactins, such as chlorfluren, chlorflurenol, dichlorflurenol, flurenol; D11) growth retardants, such as chlormequat, daminozide, flurprimidol, mefluidide, paclobutrazol, tetcyclacis, uniconazole; D12) growth stimulators, such as brassinolide, brassinolide-ethyl, DCPTA, forchlorfenuron, hymexazol, prosuler, triacontanol; D13) unclassified plant growth regulators, such as bachmedesh, benzofluor, buminafos, carvone, choline chloride, ciobutide, clofencet, cyanamide, cyclanilide, cycloheximide, cyprosulfamide, epocholeone, ethychlozate, ethylene, fuphenthiourea, furalane, heptopargil, holosulf, inabenfide, karetazan, lead arsenate, methasulfocarb, prohexadione, pydanon, sintofen, triapenthenol, trinexapac.

Plant growth promotors: E1).

Concentrates for Agricultural Compositions

The present invention also relates to a concentrate for an agricultural composition, the concentrate comprising: a) *Bacillus amyloliquefaciens* FCC1256, and b) an agriculturally suitable formulation medium, e.g. comprising a suitable carrier, a surface-active agent, and optionally a buffer.

Agricultural formulations can be obtained by proper dilution of the concentrates with a suitable liquid carrier as specified further above for the agricultural compositions, in particular an aqueous carrier. The term "aqueous carrier" is intended to mean a liquid carrier predominantly based on water and comprising up to 5% by weight of non-water constituent(s). In some embodiments, dilution is by using water only.

Typically, dilution is at a concentrate-to-carrier weight ratio of from 1:10 to 1:5000, such as from 1:20 to 1:1000.

In embodiments, the concentrate is a formulation selected from suspension concentrates (SC or SD), ultra-low volume suspensions (SU), seed treatment suspensions (FS), oil dispersions (OD), pastes (PA), gels (GD), water-dispersible granules (WG), dustable powders (DP), water-dispersible tablets (WT), water-dispersible powders for slurry treatment (WS) and wettable powders (WP).

Typically, *Bacillus amyloliquefaciens* FCC1256 is included in suitable formulations in the form of spores thereof, rather than in the form of vegetative cells. For example, the formulations may include an aliquot of a fermentation broth comprising spores of FCC1256 or a processed fermentation product comprising spores of FCC1256, such as a concentrate of a fermentation broth or a spray-dried fermentation broth.

In some embodiments, the concentrate is in liquid form, and the *Bacillus amyloliquefaciens* FCC1256 is present in the concentrate at a concentration of from $1.0 \times 10^8$ CFU/mL to $1.0 \times 10^{14}$ CFU/mL, such as from $1.0 \times 10^9$ CFU/mL to $1.0 \times 10^{13}$ CFU/mL.

In embodiments where the concentrate is in liquid form, the concentrate may be in the form of a formulation selected from suspension concentrates (SC or SD), ultra-low volume suspensions (SU), seed treatment suspensions (FS), oil dispersions (OD), pastes (PA), gels (GD), in particular suspension concentrates (SC) and oil dispersions (OD).

In other embodiments, the concentrate is in solid form, and the *Bacillus amyloliquefaciens* FCC1256 is present in the concentrate at a concentration of from $1.0 \times 10^8$ CFU/g to $1.0 \times 10^{14}$ CFU/g, such as from $1.0 \times 10^9$ CFU/g to $1.0 \times 10^{13}$ CFU/g.

In embodiments where the concentrate is in solid form, the concentrate may be in the form of a formulation selected from water-dispersible granules (WG), dustable powders (DP), water-dispersible tablets (WT), water-dispersible powders for slurry treatment (WS) and wettable powders (WP), in particular wettable powders (WP) and water-dispersible granules (WG).

In some embodiments, the concentrate comprises iturin and fengycin in a relative weight ratio of in the range of from 1.3:1.0 to 3.0:1.0, such as from 1.5:1.0 to 2.8:1.0, including all measurements within such ranges.

EXAMPLES

The following Examples have been included to provide guidance to one of ordinary skill in the art for practicing representative embodiments of the presently disclosed subject matter. Considering the present invention and the general level of skill in the art, those of skill can appreciate that the following Examples are intended to be exemplary only and that numerous changes, modifications, and alterations can be employed without departing from the scope of the presently disclosed subject matter.

Methods

Identification of Iturin, Fengycin and Surfactin

Samples were analyzed by reverse phase LC-DAD using a C18 column with a screening gradient that allowed the simultaneous detection of all three lipopeptide families. The mobile phases consisted of water and acetonitrile premixed with 0.1% formic acid. Compounds were identified based on their retention times and UV spectra compared with authentic standards.

Determination of Colony-Forming Units (CFU)

The CFU of a sample (expressed as CFU/mL for liquid samples and as CFU/g for solid samples) can be determined according to BS EN 15784:2009 ("Animal feeding stuffs. Isolation and enumeration of presumptive Bacillus spp.").

Example 1

Identification of a Bacterial Isolate as a *Bacillus Amyloliquefaciens* Through Sequence Analysis A plant associated bacterial strain, designated herein as *Bacillus amyloliquefaciens* FCC1256, was isolated from strawberry plant soil from Autryville, N.C., USA. The strain of *Bacillus amyloliquefaciens* FCC1256 was deposited on 12 May 2015 under the terms of the Budapest Treaty on the International Recognition of the Deposit of Microorganisms for the Purposes of Patent Procedure at the American Type Culture Collection (ATCC) in Manassas, Va., USA and bears the Patent Accession No. PTA-122162.

Initially, the whole genome sequence data of *Bacillus amyloliquefaciens* FCC1256 was mined to identify core phenotypic marker genes that are routinely used for phylogenetic assignment. Genes that are chosen for this analysis are both single copy, there is only one copy of the gene in the genome, and has a core housekeeping function for the cell. The six genes that were chosen from the RAST annotation file were the DNA-directed RNA polymerase beta subunit (rpoB), DNA repair recombinase A (recA 2), DNA mismatch repair protein S (mutS), glycerol uptake facilitator protein (glpF), DNA gyrase subunit B (gyrB) and DNA chaperone K (dnaK). For each of the selected genes, representative strains of genomes for the genus *Bacillus* (*Bacillus subtilis* cluster and *Bacillus cereus* cluster) were used for comparison. To that end, FCC1256 was identified as a new strain of *Bacillus amyloliquefaciens* through sequence analysis of highly conserved 16S rRNA and rpoB genes.

Also included for each gene is an outgroup sequence. These outgroup sequences are mined from genomes of phylogenetically divergent bacteria to provide an indication of the robustness of the phylogenetic calculations.

Each reference genome was first downloaded from NCBI and annotated in the RAST annotation pipeline. Each of the annotation tables generated was subsequently searched to identify each of the selected housekeeping genes and the sequences for each gene was then copied and pasted into a new nucleotide alignment in the MEGA 5.2 software program. Once each gene sequence has been loaded into the alignment all specific gene sequences were aligned using the ClustalW alignment algorithm. After each group of genes were aligned the sequences were then trimmed to ensure that each sequence had the same number of nucleotides. Following the trimming step, the aligned sequences were then used to create phylogenetic trees.

Each phylogenetic tree was replicated 1000 times to assess the robustness of the phylogenetic grouping. For each tree FCC1256 aligns and trees with other *Bacillus amyloliquefaciens* strains like DSM7, RTI301 and RTI472. These results indicate with high confidence that FCC1256 is indeed a *Bacillus amyloliquefaciens*.

The antagonistic effect of FCC1256 against a number of pathogens was also determined. Table 1 below provides a summary of the results.

TABLE 1

Antagonistic properties of *Bacillus amyloliquefaciens* FCC1256 against major plant pathogens

| Anti-Microbial Assays | FCC1256 |
|---|---|
| Fungal pathogens: | |
| *Aspergillus flavus* | ++ |
| *Botrytis cinerea* | +++ |
| *Fusarium graminearum* | +++ |
| *Fusarium oxysporum* | ++ |
| *Fusarium virguliforme* | + |
| *Phytophthora capsici* | + |
| *Rhizoctonia solani* | ++ |
| Bacterial pathogens: | |
| *Erwinia amylovora* | ++ |
| *Xanthomonas euvesicatoria* | ++ |

+++ very strong activity,
++ strong activity,
+ activity,
+− weak activity,
− no activity observed In addition, experiments were performed to determine the antagonistic activities of *Bacillus amyloliquefaciens* FCC1256 in vitro and in various plants under varying conditions. The experimental results are provided in Examples 3, 5, 6 and 7 below.

The experiments i.a. show the ability of *Bacillus amyloliquefaciens* FCC1256 to confer protection against or control plant pathogenic infection as compared to commercially available Serenade® (Bayer CropScience, Inc.) that contains as an active ingredient *Bacillus velezensis* QST713.

Example 2

Fermentation of *Bacillus Amyloliquefaciens* FCC1256

*Bacillus amyloliquefaciens* FCC1256 was first streaked out from a glycerol stock onto a solid 869 media, which contained (in 1 L): 10 g tryptone, 5 g yeast extract, 1 g D-glucose, 0.3 g $CaCl_2$, and 15 g powdered agar. After incubating at 30° C. overnight, a single colony was picked up to inoculate a 250-mL shake flask with 50 mL of media containing (in 1 L): 10 g peptone, 6 g yeast extract, 2 g KCl, and 0.1 g $MgSO_4.7H_2O$. After autoclaving, the following solutions were added to the medium: 5 mL of 20% glucose, 1 mL of 1M $CaCl_2$, 1 mL of 0.1 M $MnCl_2$, and 10 µL of 0.1 M $FeSO_4$. The shake flask was incubated in a shaking incubator at 30° C. and 200 rpm until the OD600 reached 1.0. The cell pellets were collected for the inoculation of fermenters (working volume 1.5 L, Bioflo 320, Eppendorf). The fermentation was made at 30° C., agitation speed was 800 rpm, and the air supply rate was 2 L/min. Samples were taken during the fermentation to monitor cell growth, cell sporulation, and metabolite concentrations. After 168 hours of fermentation, most of the *Bacillus amyloliquefaciens* FCC1256 cells had sporulated, and the whole culture mixture was harvested.

*Bacillus amyloliquefaciens* FCC1256 and reference strain QST713 (a *Bacillus velezensis* strain obtained from a commercial Serenade® product) were fermented in the above-mentioned culture medium. Using the OD600 measurement, the biomass levels during fermentation were measured. A comparison of the metabolite profiles for the *Bacillus amyloliquefaciens* FCC1256 strain and QST713 showed that FCC1256 produced iturin at a significantly higher rate than QST713 under the same conditions.

Further evaluation of the metabolite concentrates revealed that FCC1256 had an iturin:fengycin:surfactin weight ratio at about 3.3:1.4:1, potentially contributing to the antagonistic activities of the strain against plant pathogens.

Example 3

Anti-Microbial Properties of *Bacillus Amyloliquefaciens* FCC1256

*Bacillus amyloliquefaciens* FCC1256, and QST713 were plated and grown in TSA plates overnight (16-18 h) at 30° C. Following, a single colony was transferred in medium (growth medium $H_2O$, 914.3 mL; $NH_4NO_3$, 8 g; $Na_2HPO_4$, 7.15 g; $KH_2PO_4$, 6.8 g; yeast extract 0.5 g; adjusted to 7.5 with 4 mL 4 M KOH; 45 mL of the growth medium were transferred to a 250-mL baffled flasks and autoclaved at 121° C. for 15 min. After autoclaving the following solutions were added in each flask: 0.1 M $CaCl_2$ 5 µL, 0.1M $MnCl_2$ 5 µL, 0.1M $FeSO_4$ 35 µL, 0.1M $ZnCl_2$ 5 µL, 1M $MgSO_4$ 100 glucose 50% sol (final conc. 40 g/L) 4 mL) and incubated for 168 h at 30° C. and under continuous agitation (220 rpm). The strains were grown in 250-mL baffled flasks with GL 45 thread (Duran®, Germany) and 50 mL final working volume.

In total, 14 foliar plant pathogens (12 fungi and 2 bacteria) were used during this study. Specifications of the pathogens, the growth conditions and media used are shown in Table 2. All foliar pathogens used for this experiment were tested in Potato Dextrose Agar (PDA) solid medium except *Pseudomonas syringae* and *Xanthomonas axonopodis* which were tested in Trypticase soy agar (TSA) solid medium. The incubation time of each pathogen before treatment varied from 3 to 5 days. In case of *Pseudomonas syringae* and *Xanthomonas axonopodis* where lawn plates are used for testing, an overnight culture on 869 media was prepared while *Septoria tritici* was cultured on Potato Dextrose Broth for 5 days before lawn preparation.

The activity was assessed by the application of 20 µL of cells. All applications were conducted in triplicates for all pathogens using the fermented material non-filtered. Rating timings for fungal pathogens vary by species. Timing should correspond to the colony edge reaching a radius of approximately 25 mm on the control spot plates. For the assessment, a semi-quantitative method was used, cf. the following 4-scale system (0-3) where: 0: no antimicrobial effect seen; 1: slight effect caused but no obvious clearing zone; 2: a clearing zone is obvious; 3: large clearing zone is present. The results are shown in Table 2.

TABLE 2

Anti-microbial properties of FCC1256 against foliar pathogens

| Genus and species | Incubation conditions | Transfer type | Days of incubation before/after treatment | Rating QST713 | Rating FCC1256 |
| --- | --- | --- | --- | --- | --- |
| *Botrytis cinerea* (Bc) | Dark, 22° C. | Agar plug | 0/4 | 2 | 2 |
| *Stagnospora nodorum* (Sn) | Dark, 22° C. | Agar plug | 0/6 | 2 | 2 |
| *Septoria tritici* (St) | Dark, 22° C. | Agar plug | 5/6 | 2 | 3 |
| *Fusarium oxysporum* (Fo) | Dark, 22° C. | Agar plug | 0/4 | 2 | 1 |
| *Fusarium graminearum* (Fg) | Dark, 22° C. | Agar plug | 0/4 | 2 | 3 |
| *Fusarium culmorum* (Fc) | Dark, 22° C. | Agar plug | 0/4 | 2 | 2 |
| *Monilina fructicola* (Mf) | Dark, 22° C. | Agar plug | 0/4 | 2 | 3 |
| *Sclerotinia homeocarpa* (Sh) | Dark, 22° C. | Agar plug | 0/3 | 2 | 3 |
| *Pyrenophora teres* (Pt) | Dark, 22° C. | Agar plug | 0/4 | 2 | 3 |
| *Alternaria solani* (As) | Dark, 22° C. | Agar plug | 0/6 | 2 | 3 |
| *Magnaporthe oryzae* (Mo) | Dark, 22° C. | Agar plug | 0/6 | 2 | 3 |
| *Glomerella cingulata* (Gc) | Dark, 22° C. | Agar plug | 0/4 | 2 | 3 |
| *Pseudomonas syringae* (Pss) | Dark, 30° C. | Lawn | 1/2 | 1 | — |
| *Xanthomonas axonopodis* (Xa) | Dark, 30° C. | Lawn | 1/2 | 2 | 2 |

Example 4

Phenotypic Traits of *Bacillus Amyloliquefaciens* FCC1256

In addition to the antagonistic properties, various phenotypic traits were also measured for *Bacillus amyloliquefaciens* FCC1256 and the data are shown below in Table 3. The assays were performed according to the procedures described in the text below Table 3.

TABLE 3

Phenotypic Assays: phytohormone production, acetoin and indole acetic acid (IAA), and nutrient cycling of *Bacillus amyloliquefaciens* FCC1256.

| Characteristic Assays | FCC1256 |
|---|---|
| Acetoin production (MR-VP) | +++ |
| Chitinase activity | + |
| Indole-3-Acetic Acid production | − |
| Protease activity | ++ |
| Phosphate solubilization | + |

+++ very strong,
++ strong,
+ some,
+− weak,
− none observed

Acetoin Test. 20 µL of a starter culture in media was transferred to 1 mL Methyl Red Voges Proskauer media (Sigma Aldrich 39484). Cultures were incubated for 2 days at 30° C. 200 rpm. 0.5 mL culture was mixed with 0.3 mL 5% alpha-naphthol (Sigma Aldrich N1000) followed by 0.1 mL 40% KOH. Samples were interpreted after 30 min. of incubation. Development of a red color indicated acetoin production. Non-inoculated media was used as a negative control (Sokol et al., 1979, *Journal of Clinical Microbiology* 9: 538-540).

Chitinase activity. 10% wet weight colloidal chitin was added to modified PVK agar medium (10 g glucose, 0.2 g potassium chloride, 0.5 g ammonium sulfate, 0.2 g sodium chloride, 0.1 g magnesium sulfate heptahydrate, 0.5 g yeast extract, 2 mg manganese sulfate, 2 mg iron sulfate and 15 g agar per liter, pH 7, autoclaved). Bacteria were plated on these chitin plates; zones of clearing indicated chitinase activity (N. K. S. Murthy & Bleakley, 2012. "Simplified Method of Preparing Colloidal Chitin Used for Screening of Chitinase Producing Microorganisms". *The Internet Journal of Microbiology* 10(2)).

Indole-3-Acetic Acid. 20 µL of a starter culture in media was transferred to 1 mL 1/10 869 media supplemented with 0.5 g/L tryptophan (Sigma Aldrich T0254). Cultures were incubated for 4-5 days in the dark at 30° C., 200 rpm. Samples were centrifuged and 0.1 mL supernatant was mixed with 0.2 mL Salkowski's Reagent (35% perchloric acid, 10 mM $FeCl_3$). After incubating for 30 min. in the dark, samples resulting in pink color were recorded positive for IAA synthesis. Dilutions of IAA (Sigma Aldrich I5148) were used as a positive comparison; non-inoculated media was used as negative control (Taghavi, et al., 2009, *Applied and Environmental Microbiology* 75: 748-757).

Protease Activity. Bacteria were plated on 869 media supplemented with 10% milk. Clearing zones indicated the ability to break down proteins suggesting protease activity (Sokol et al., 1979, *Journal of Clinical Microbiology* 9: 538-540).

Phosphate Solubilizing Test. Bacteria were plated on Pikovskaya (PVK) agar medium consisting of 10 g glucose, 5 g calcium triphosphate, 0.2 g potassium chloride, 0.5 g ammonium sulfate, 0.2 g sodium chloride, 0.1 g magnesium sulfate heptahydrate, 0.5 g yeast extract, 2 mg manganese sulfate, 2 mg iron sulfate and 15 g agar per liter, pH 7, autoclaved. Zones of clearing were indicative of phosphate solubilizing bacteria (Sharma et al., 2011, *Journal of Microbiology and Biotechnology Research* 1: 90-95).

Example 5

*Bacillus Amyloliquefaciens* FCC1256 Antagonism on Pepper Grey Mold (*Botrytis Cinerea*)

Studies were performed in the greenhouse on pepper to determine the ability of FCC1256 to prevent and/or ameliorate the effects of the plant pathogen Pepper Grey Mold (*Botrytis cinerea*).

Formulations:

Isolated spores of FCC1256 were formulated in 100% spent fermentation broth (SFB) at a concentration of $1 \times 10^8$ CFU/mL (i.e. a reconstituted fermentation broth concentrate). A similar FCC1256 formulation was prepared but with added nutrients (2 g sucrose+1.5 g yeast extract+0.2 g $MgSO_4.7H_2O$ per liter).

Isolated spores of *Bacillus amyloliquefaciens* RTI472 were similarly formulated in 100% spent fermentation broth (SFB) at a concentration of $1 \times 10^8$ CFU/mL. A similar RTI472 formulation was prepared by with added nutrients (as above for FCC1256).

Serenade® Optimum (Bayer CropScience, Inc.) was applied at a spore concentration of $1 \times 10^8$ CFU/mL.

Horizon (Horizon AG-Products) was applied at a rate of 50 g a.i./ha (Tebuconazole).

Treatment Application Method:

A track sprayer was used to inoculate 28 days old pepper plants in a greenhouse with each of the formulations described above. The track sprayer had a single overhead nozzle (TeeJet SS8001E Flat Fan) at a pressure of 276 kPa (40 psi). The nozzle height was 36 cm (14") above the pepper plant leaves. The application volume was 200 L/ha and the number of repetitions in the experiment equaled six. The treatment plants were inoculated a single time along with control plants not receiving any treatment.

Infection Rate:

One day following treatment application, the test plants were infected with *Botrytis cinerea* at an infection rate of 500,000 conidia/mL.

Three days following infection with Pepper Grey Mold (*Botrytis cinerea*) the percent of disease control (mean) was evaluated for each of the above-described formulations.

The results of the experiment are shown in Table 4 below and indicate a superior control of Pepper Grey Mold (*Botrytis cinerea*) as compared to RTI472 and Serenade® Optimum when applied at the same rate.

TABLE 4

Results of *B. amyloliquefaciens* FCC1256 control of Pepper Grey Mold (*Botrytis cinerea*) as compared to Serenade ® Optimum and other references.

| Treatment (each $1 \times 10^8$ CFU/mL) | Percent Disease Control |
|---|---|
| FCC1256 + 100% SFB | 98 (±1) |
| FCC1256 + 100% SFB + nutrients | 98 (±1) |
| Nutrients | 0 |
| RTI472 + 100% SFB | 96 (±1) |
| RTI472 + 100% SFB + nutrients | 87 (±4) |
| Serenade ® Optimum | 90 (±2) |
| Horizon | 100 (±0) |

Example 6

*Bacillus Amyloliquefaciens* FCC1256 Antagonism on Pepper *Phytophthora* Blight

Studies were performed in the greenhouse on pepper to determine the ability of FCC1256 to prevent and/or ameliorate the effects of the plant pathogen Pepper *Phytophthora* Blight (*Phytophthora capsici*).

Formulations:

Isolated spores of FCC1256 were formulated in 100% spent fermentation broth (SFB) at a concentration of $1 \times 10^8$ CFU/mL (i.e. a reconstituted fermentation broth concentrate). A similar FCC1256 formulation was prepared but with added nutrients (2 g sucrose+1.5 g yeast extract+0.2 g $MgSO_4.7H_2O$ per liter).

Isolated spores of *Bacillus amyloliquefaciens* RTI472 were similarly formulated in 100% spent fermentation broth (SFB) at a concentration of $1\times10^8$ CFU/mL. A similar RTI472 formulation was prepared by with added nutrients (as above for FCC1256).

Serenade® Soil (Bayer CropScience, Inc.) was applied at a spore concentration of $1\times10^8$ CFU/mL.

Ridomil Gold (Syngenta, Inc.) was applied at a rate of 0.5 lb a.i./acre (mefenoxam).

Treatment Application Method:

The soil of 28 days old pepper plants was drenched with 10 mL of water containing each of the formulations described above. The number of repetitions in each experiment equaled six. The treatment plants were inoculated a single time along with control plants not receiving any treatment.

Infection Rate:

For each of the studies, on the same day as treatment application, the test plants were infected with *Phytophthora capsici* FF157 at a rate of 1 mL of 1,000 zoospores/mL.

Eight days following infection of the plants with Pepper *Phytophthora* Blight (*Phytophthora capsici*) the percent of disease control was evaluated for each of the treatments. The disease severity score was 9.8 (0=healthy; 10=dead) at 8 days following infection.

The results showed a statistically superior control of Pepper *Phytophthora* Blight by the FCC1256 as compared to Serenade® Soil when applied at the same rate.

TABLE 5

Results of *Bacillus amyloliquefaciens* FCC1256 control of Pepper *Phytophthora* Blight as compared to Serenade ® Optimum.

| Treatment | Percent Disease Control |
|---|---|
| FCC1256 + 100% SFB | 79 (±14) |
| FCC1256 + 100% SFB + nutrients | 44 (±18) |
| Nutrients | 6 (±6) |
| RTI472 + 100% SFB + nutrients | 6 (±6) |
| Ridomil Gold | 100 (±0) |
| Serenade ® Soil | 30 (±8) |

Example 7

Detached Pepper Leaf Disk Assay Comparing the Activity of *Bacillus Amyloliquefaciens* FCC1256 to Untreated Controls as Well as to the Commercial Product Serenade® Optimum.

Pepper (*Piper capsicum*) plants were grown in greenhouse at 20-25° C. with 14-16 hours daylight for 6-7 weeks. From each plant, four fully expanded leaves from the middle part were harvested and put in petri dishes with moist filter paper. Leaves were sprayed with water (untreated control) or suspension of Serenade® Optimum (positive control) or FCC1256 fermentates (two different batches). Then lids were put on thee petri dishes and placed for incubation in a growth chamber set at approx. the same growth conditions as the greenhouse.

The following day the leaves were inoculated by spraying with a spore suspension of *Botrytis cinerea*, adjusted to 500,000 spores/mL. Then the petri dishes were put back in the growth chamber and evaluated after 4 days, 6 days and 9 days to follow the progression of the disease.

The results are shown in FIG. 1. Column 1 shows the Serenade Optimum reference (application equivalent of 2.8 kg/ha); Column 2 shows the untreated inoculated control; Column 3 shows the untreated uninoculated control, Columns 4 and 5 show *Bacillus amyloliquefaciens* FCC1256 of two different fermentation batches. Rows 1 and 2 show results 4 days post inoculation. Rows 5 and 6 show the same leaves but 6 days post inoculation, and rows 3 and 4 show again the same leaves but 9 days post inoculation.

By visual inspection it is clearly see that the leaves of the untreated inoculated control (column 2) were highly damaged even after 4 days, and that the leaves of the untreated uninoculated control (column 3) remained fresh throughout the 9 days experiment. The Serenade® Optimum reference showed some pathogen control after 3 days, by the leaves were highly damaged after 6 and 9 days. On the other hand, the FCC1256 fermentates showed very good pathogen control after 4 and 6 days, and acceptable control after 9 days.

Example 8

(a) Concentrate of *Bacillus Amyloliquefaciens* FCC1256

A concentrate of FCC1256 was prepared as follow: 20% FCC1256 fermentate concentrate, 45% water, 30% glycerin (86.5%), 5% Marasperse AG (sodium lignosulfonate; anionic dispersant) were mixed, pH was adjusted to 6.0-7.5 using a $HK_2PO_4.H_2O/KH_2PO_4$ buffer. The spore content (FCC1256) of the final composition was typically in the range of $1.0\times10^{10}$ CFU/mL to $1.0\times10^{12}$ CFU/mL.

(b) Concentrate of *Bacillus Amyloliquefaciens* FCC1256

A composition of FCC1256 was prepared as follow: 50% FCC1256 fermentate concentrate, 4.8% water, 40% glycerin (86.5%), 5% Marasperse AG (sodium lignosulfonate; anionic dispersant), 0.1% antifoam and 0.1% Kelzan (thickener) were mixed, pH was adjusted to 6.0-7.5 using a $HK_2PO_4.H_2O/KH_2PO_4$ buffer. The spore content (FCC1256) of the final composition was typically in the range of $1.0\times10^{10}$ CFU/mL to $1.0\times10^{12}$ CFU/mL.

(c) Agricultural Composition of *Bacillus Amyloliquefaciens* FCC1256

A concentrate of (a) or (b) as specified above was diluted with water at a ratio of 1:12 to produce an agricultural composition. The composition was applicable for application as at rate of e.g. 200-600 L/ha.

Example 9

Whole Plant Pepper Assay Comparing the Antifungal Activity of *Bacillus Amyloliquefaciens* FCC1256 Against Pepper Grey Mold (*Botrytis Cinerea*) to Untreated Controls as Well as to Other *Bacillus Amyloliquefaciens* Strains Four different *Bacillus amyloliquefaciens* strains, FCC1256, DSM7, RTI472 and RTI301, were fermented under similar conditions (cf. Example 2), except that the fermentations were conducted in a smaller scale using 500 mL shake flasks with 60 mL culture. The growing temperature was 28° C., the agitation was 200 rpm and the incubation time was 144 hours. The fermentations each provided a spore concentration in the order of $1\times10^7$ CFU/mL.

Pepper plants (*Piper capsicum* variety Lamuyo F1) were produced in 7×7×7 cm plastic pots, using Agrofino 201 soil substrate. They were aged of 6 weeks at the time of the test. Watering of the plants was provided every two days using fertilization of N:P:K=20:20:20 at 160 ppm. Six replicates were used per tested modality, each replicate consisting in 1 plant (1 pot).

Each plant was treated inside a laboratory sprayer using a 3-nozzle boom at an estimated volume of 1000 L/ha. Each of the four different *Bacillus amyloliquefaciens* strains, FCC1256, DSM7, RTI472 and RTI301, were used at a dose of 20 mL of fermentation broth diluted in 100 mL of demineralized water and was mixed with 0.2% vol/vol of an adjuvant mixture. The fermentation medium with the 0.2% vol/vol adjuvant mixture and without *Bacillus* strain was also evaluated as a reference.

After application, plants were stored in growth chamber at 20° C., 70% RH and 16 hours photo-period. Inoculation was carried out 24 hours after fungicide application, by manually spraying inoculum of *Botrytis cinerea* on treated plants up to run-off. Inoculum concentration was 50,000 spores/mL inside PDB medium (strain of *Botrytis cinerea* FF248). After inoculation, plants were stored for 48 hours in a dew chamber at 20° C. (no light) to favor infection. Plants were then place in a growth chamber at 20° C., 70% RH and 16 hours photo-period, up to disease rating.

Disease assessment was done three days after inoculation, by evaluating % severity on four fully developed leaves per plant. The averaged % severity per pot was then calculated (reported in Table 6), and the efficacy of the tested strains was calculated using Abott formula:

% control$A$=100*((% severity$A$−% severity untreated)/% severity untreated)

TABLE 6

Results of *Bacillus amyloliquefaciens* FCC1256 control of Pepper Grey Mold (*Botrytis cinerea*) as compared with *Bacillus amyloliquefaciens* strains RTI301, DSM7 and RTI472.

| Strain | Percent Disease control |
| --- | --- |
| RTI301 | 26 (±26) |
| DSM7 | 72 (±10) |
| RTI472 | 83 (±11) |
| FCC1256 | 94 (±6) |
| Fermentation medium (reference) | 3 (±5) |
| Untreated (control) | 0 (±0) |

REFERENCES

All publications, patent applications, patents, and other references mentioned in the specification are herein incorporated by reference in their entireties.

Although the foregoing subject matter has been described in some detail by way of illustration and example for purposes of clarity of understanding, it will be understood by those skilled in the art that certain changes and modifications can be practiced within the scope of the appended claims.

We claim:

1. A method of controlling at least one fungal plant pathogen on a plant, the method comprising applying a composition comprising *Bacillus amyloliquefaciens* FCC1256 deposited as ATCC No. PTA-122162 to the plant, to a part of the plant and/or to a locus at which the plant or plant part grows or is to be planted.

2. The method of claim 1, wherein the composition is in liquid form, and wherein the *Bacillus amyloliquefaciens* FCC1256 is present in the composition at a concentration of from $1.0 \times 10^6$ CFU/mL to $1.0 \times 10^{12}$ CFU/mL.

3. The method of claim 1, wherein the composition is in the form of a liquid formulation selected from suspensions, suspension concentrates (SC), oil dispersions (OD) and foams.

4. The method of claim 1, wherein the composition is in solid form, and wherein the *Bacillus amyloliquefaciens* FCC1256 is present in the composition at a concentration of from $1.0 \times 10^6$ CFU/g to $1.0 \times 10^{12}$ CFU/g.

5. The method of claim 1, wherein the composition is in the form of a solid formulation selected from dustable powders (DP), water-dispersible granules (WG) and wettable powders (WP).

6. The method of claim 1, wherein the composition is applied at a rate of from $4.0 \times 10^9$ CFU/ha to $4.0 \times 10^{17}$ CFU/ha.

7. The method of claim 1, wherein the at least one plant pathogen is selected from the group consisting of *Botrytis cinerea, Botrytis squaomas, Fusarium graminearum, Fusarium oxysporum, Fusarium viguliforme, Phytophthora infestans, Phytophthora parasitica, Phytophthora sojae, Phytophthora capsici, Phytophthora cinnamomi, Phytophthora fragariae, Phytophthora ramorum, Phytophthora palmivara, Phytophthora nicotianae, Sclerotinia sclerotiorum, Sclerotinia minor, Sclerotinia homeocarpa, Aspergillus Favus, Rhizoctonia solani,* and any combinations thereof.

8. The method of claim 1, wherein the plant is selected from pepper, cucumbers, apples, asparagus, berries, bananas, citrus, kiwi, melons, peaches, pears, pineapple, pome fruit, pomegranate, celery, onions, garlic, grapes, leeks, shallots, chives, broccoli, cabbage, cauliflower, cucurbits, tomatoes, potatoes, wheat, rice and soybeans.

9. The method of claim 8, wherein the berries comprise blueberry, blackberry, raspberry, loganberry, huckleberry, cranberry, gooseberry, elderberry, currant, cane berry, bush berry, strawberry, bayberry, bearberry, highbush blue berry, lowbush blue berry, chokecherry, lingonberry, mulberry, pin cherry, Salaberry, Saskatoon berry, sea buckthorn or wild raspberry.

10. The method of claim 1, wherein the composition comprises iturin and fengycin in a relative weight ratio in the range of from 1.3:1.0 to 3.0:1.0.

11. The method of claim 1, wherein the composition further comprises an agriculturally suitable formulation medium comprising a suitable carrier, a surface-active agent, and optionally a buffer.

12. The method of claim 1, wherein the composition has further antimicrobial activity against bacterial pathogens selected from the group consisting of *Erwinia* amylovara, and *Xanthomonas* euvesicatoria, and combinations thereof.

13. An agricultural composition comprising:
   a) a fermentation broth comprising spores of *Bacillus amyloliquefaciens* FCC1256 deposited as ATCC No. PTA-122162 or a processed fermentation product comprising spores of *Bacillus amyloliquefaciens* FCC1256 deposited as ATCC No. PTA-122162, and
   b) an agriculturally suitable formulation medium comprising a suitable carrier, a surface-active agent, and optionally a buffer.

14. The composition of claim 13, comprising iturin and fengycin in a relative weight ratio in the range of from 1.3:1.0 to 3.0:1.0.

15. The composition of claim 13, wherein the composition is a formulation selected from suspensions, suspension concentrates (SC), oil dispersions (OD), foams, dustable powders (DP), water-dispersible granules (WG) and wettable powders (WP).

16. A concentrate for an agricultural composition, the concentrate comprising:
   a) a fermentation broth comprising spores of *Bacillus amyloliquefaciens* FCC1256 deposited as ATCC No. PTA-122162 or a processed fermentation product comprising spores of *Bacillus amyloliquefaciens* FCC1256 deposited as ATCC No. PTA-122162, and b) an agriculturally suitable formulation medium comprising a suitable carrier, a surface-active agent, and optionally a buffer.

17. The concentrate of claim 16, which is in the form of a formulation selected from suspension concentrates (SC or SD), ultra-low volume suspensions (SU), seed treatment suspensions (FS), oil dispersions (OD), pastes (PA), gels (GD), water-dispersible granules (WG), dustable powders (DP), water-dispersible tablets (WT), water-dispersible powders for slurry treatment (WS) and wettable powders (WP).

18. The concentrate of claim 16, comprising iturin and fengycin in a relative weight ratio in the range of from 1.3:1.0 to 3.0:1.0.

* * * * *